United States Patent [19]

Kaplan

[11] Patent Number: 4,522,807

[45] Date of Patent: Jun. 11, 1985

[54] SUBSTANTIVE TOPICAL COMPOSITIONS

[75] Inventor: Carl Kaplan, Memphis, Tenn.

[73] Assignee: Plough, Inc., Memphis, Tenn.

[21] Appl. No.: 496,032

[22] Filed: May 19, 1983

Related U.S. Application Data

[63] Continuation-in-part of Ser. No. 342,304, Jan. 25, 1982, abandoned.

[51] Int. Cl.$^3$ .................... A61K 7/42; A61K 7/44
[52] U.S. Cl. ........................ 424/59; 424/47; 424/60; 514/159; 514/543; 514/567
[58] Field of Search .................... 424/59, 60

[56] References Cited

U.S. PATENT DOCUMENTS

| | | | |
|---|---|---|---|
| 3,019,162 | 11/1962 | Brunner et al. | 424/60 |
| 3,186,912 | 6/1965 | Beamer | 424/60 |
| 3,452,044 | 6/1969 | Levine et al. | 424/60 X |
| 3,729,451 | 4/1973 | Blecke et al. | 260/203 |
| 3,846,546 | 11/1974 | Lachampt et al. | 424/170 |
| 3,860,700 | 1/1975 | Viout et al. | 424/61 |
| 3,895,104 | 7/1975 | Karg | 424/59 |
| 3,937,811 | 2/1976 | Papantonion | 424/59 |
| 4,316,902 | 2/1982 | Yu et al. | 424/60 |

OTHER PUBLICATIONS

Brown, Household & Personal Products Industry, 5/1980, pp. 1 to 4.
American Hospital Formulary Service, 1965, vol. 2, pp. 68:04.

*Primary Examiner*—Dale R. Ore
*Attorney, Agent, or Firm*—Gerald S. Rosen; Warrick E. Lee, Jr.; Stephen I. Miller

[57] ABSTRACT

A highly substantive topical composition in the form of an oil-in-water emulsion containing an octadecene-1/maleic anhydride copolymer.

14 Claims, No Drawings

SUBSTANTIVE TOPICAL COMPOSITIONS

This is a continuation-in-part of U.S. application Ser. No. 342,304, filed Jan. 25, 1982, now abandoned.

This invention relates to dermatologically acceptable, highly substantive, topical oil-in-water emulsions containing an octadecene - 1/maleic anhydride copolymer. They are particularly useful as vehicles for sunscreen compositions.

BACKGROUND OF THE INVENTION

There has been a long recognized need for a cosmetic or medicinal vehicle which is highly substantive, i.e., highly resistant to removal by water. Such a vehicle would be of particular interest in a sunscreen composition for use by bathers or any other person whose occupation or life-style made it necessary to be exposed to the actinic rays of the sun.

Many of the sunscreen compositions which have been known heretofore have been easily removed by water. Thus, repeated applications of the product become necessary for persons who swim, remain in the water outdoors for extended periods, or perspire freely.

The vehicles of this invention are also useful in medicinal emulsions for the topical application of certain dermatologically compatible medicaments, particularly anti-inflammatory steroids, e.g. betamethasone valerate and betamethasone dipropionate. These medicaments find widespread use during the summer months when inflammation causing insects (e.g. bees) and plants (e.g. poison ivy) are at their peak and a user is more likely to perspire freely or swim.

We have surprisingly found that one can prepare a highly substantive oil-in-water emulsion by incorporating therein a polyanhydride resin derived from octadecene-1 and maleic anhydride. The copolymers can be made by published methods such as those shown in U.S. Pat. No. 3,729,451.

The preferred polyanhydride copolymer is linear, has a molecular weight of 4,000–100,000, more preferably 40,000–60,000, and has the comonomers present in essentially a 1:2 to 2:1 molar ratio.

A most preferred copolymer is commercially available from Gulf Oil Chemicals Company under the tradename of PA-18. PA-18 is a solid, linear polyanhydride resin having a molecular weight of about 50,000, a specific gravity of 0.97, and a melting point range of 110°–120°. The name given to PA-18 in the Third Edition of the CTFA Cosmetic Ingredient Dictionary is Octadecene/Maleic Anhydride Copolymer. This preferred copolymer was generally recognized as an emulsion stabilization agent in water-in-oil emulsion systems in U.S. Pat. Nos. 3,846,546 and 3,860,700. It has not, however, heretofore been recognized as a substantivity improving agent in oil-in-water emulsion systems.

The preferred sunscreen compositions are anionic oil-in-water emulsions having a pH of about 6 to 10, preferably 7 to 9, and in which the polyanhydride copolymer is present at a concentration of about 0.01 to 5.0 percent, more preferably about 0.3 to 3.0 percent.

The preferred anionic emulsifiers in a sunscreen composition are the soaps formed from a fatty acid and an amine or alkali, e.g. stearic acid and triethanolamine; the reaction products of ethylene maleic anhydride copolymers and an amine or alkali, e.g. the EMA-91 resin sold by Monsanto and described in U.S. Pat. No. 3,821,363 with sodium hydroxide; and the reaction products of the polymers of acrylic acid cross-linked with a polyfunctional agent and an amine or alkali, e.g. carbomer 940 and triethanolamine.

The preferred medicament formulas containing an anti-inflammatory steroid are preferably nonionic oil-in-water compositions having a pH of 4 to 9, more preferably a pH of 4 to 6, and a polyanhydride copolymer concentration of 0.01 to 0.5 percent, more preferably 0.01 to 0.1 percent.

The sunscreen compositions of this invention all contain sunscreen agents which are effective in low concentrations and are generally of low solubility in water. Suitable sunscreen agents include the esters of para-aminobenzoic acid, and substituted para-aminobenzoic acid, e.g. octyl dimethyl PABA; certain esters of salicylic acid, e.g. homomenthyl salicylate; certain benzophenone derivatives, e.g. benzophenone-3; and the esters of para-methoxycinnamic acid, e.g. octyl methoxycinnamate.

Various optional ingredients may be included in the formulation, such as perfumes; preservatives, e.g. parabens and imidazolidinyl urea; emollients, e.g, lanolin, cocoa butter; antiseptics; pigments; dyes; propellants; foaming agents; viscosity control agents; as well as any other class of materials whose presence may be cosmetically, medicinally or otherwise desirable.

The remainder of the composition would consist essentially of water which would generally be in a concentration of 40–95 percent, preferably 60–90 percent. It is, of course, understood that water is the external phase of an oil-in-water emulsion.

The following examples illustrate the invention. The terminology used in the examples and throughout the specification is in conformance with the *CTFA Cosmetic Ingredients Dictionary*, Second Edition, The Cosmetics, Toiletries and Fragrance Association, Washington, D.C., 1977. All proportions, unless otherwise specified are by weight.

EXAMPLE I

A topical substantive sunscreen composition was prepared according to the following formulation:

|  | Weight Percent |
| --- | --- |
| Part A |  |
| Homomenthyl Salicylate | 9.0 |
| Octadecene/Maleic Anhydride Copolymer | 0.4 |
| Glyceryl Dilaurate | 2.5 |
| Glyceryl Stearate SE | 2.5 |
| Propylparaben | 0.05 |
| Part B |  |
| Water | 60.0 |
| Ethylene/Maleic Anhydride Copolymer | 0.25 |
| Methylparaben | 0.1 |
| Part C |  |
| Water | 23.0 |
| Part D |  |
| Imidazolidinyl Urea | 0.1 |
| Part E |  |
| Fragrance | 0.3 |
| Part F |  |
| Sodium Hydroxide, U.S.P. Pellets | 0.18 |
| Water | 1.62 |

The ingredients of Part A (oil phase) are heated and agitated at 82°–85° until all of the ingredients have melted or dissolved. The mixture is then cooled to 49°–52° C.

The ingredients of Part B are heated and agitated at 85°–91° C. until uniformity results. The water from Part C is added to Part B and the mixture cooled to about 67° C. Agitation is continued and the mixture is further cooled to about 49°–52° C. Part D is then added to the mixture of Parts B and C. The ingredients of Part A and the fragrance of Part E are added to the mixture until uniformity results.

The sodium hydroxide solution of Part F is added to the mixture and the batch is run through a colloid mill. The resulting mixture will have a pH of 7.5 to 8.5.

A sunscreen composition prepared according to the above example was tested on hairless mouse epidermis and found to be highly substantive. The standard protection factor (SPF) is a measure of how well a composition protects skin from the rays of the sun. The higher the SPF, the better the protection. The static SPF is a measure of how well a composition protects after application to the skin and air drying, i.e. without exposure to running water. The static SPF and the SPF of the composition after 10 and 40 minutes exposure to running water were tested with the following results:

| | |
|---|---|
| Static SPF | 3.3 ± 0.91 |
| SPF after 10 minute exposure to running water | 2.8 ± 0.45 |
| SPF after 40 minute exposure to running water | 3.0 ± 1.0 |

EXAMPLE II

A topical composition was prepared in a manner similar to Example I

| Ingredient | Weight Percent |
|---|---|
| Lanolin | 4.5 |
| Cocoa Butter | 2.0 |
| Glyceryl Stearate SE | 3.0 |
| Stearic Acid | 2.0 |
| Octadecene/Maleic Anhydride Copolymer | 1.0 |
| Octyl Dimethyl PABA | 7.0 |
| Benzophenone-3 | 3.0 |
| Sorbitol | 5.0 |
| Triethanolamine | 1.0 |
| Carbomer 940 | .05 |
| Benzyl Alcohol | 0.5 |
| Fragrance | 0.075 |
| Water | q.s |

A sunscreen composition prepared according to the above formula was found to highly substantive when tested on hairless mouse epidermis. Formulas similar to Example II but having concentrations of the octadecene/maleic anhydride copolymers as low as 0.01 percent were still found to be highly substantive when tested on hairless mouse epidermis:

| % octadecene-1/maleic anhydride copolymer | SPF after allowing formulation to air dry on the skin (Static SPF) | SPF after 10 minute exposure to running water | SPF after 40 minute exposure to running water |
|---|---|---|---|
| 0.01 | 3.9 | 5.5 | 5.5 |
| 0.025 | 4.8 | 7.5 | 6.9 |
| 0.125 | 5 | 8 | 12 |
| 0.25 | 5.4 | 6.8 | 8.8 |
| 0.50 | 6.2 | 8.4 | 10.0 |
| 1.00 | 7.3 | 8.6 | 11.7 |
| 4.00 | 9.1 | 8.5 | 7.6 |

EXAMPLE III

A topical substantive sunscreen composition was prepared according to the following formulation:

| | Parts By Weight |
|---|---|
| Part A | |
| Octyl dimethyl PABA | 6 |
| Octadecene/maleic anhydride copolymer | 1 |
| Glyceryl Dilaurate | 2.5 |
| Glyceryl Stearate SE | 2.5 |
| Propylparaben | 0.1 |
| Benzophenone-3 | 2 |
| Sorbitan sesquioleate | 2 |
| Part B | |
| Water | 60 |
| Ethylene/Maleic Anhydride Copolymer | 0.25 |
| Methylparaben | 0.2 |
| Part C | |
| Water | 22.53 |
| Part D | |
| Imidazolidinyl urea | 0.1 |
| Part E | |
| Fragrance | 0.6 |
| Part F | |
| Sodium hydroxide, U.S.P. Pellets | 0.22 |
| Water | 1.98 |

The ingredients were combined in accordance with the procedure of Example I.

This emulsion was applied to the backs of 7 human volunteers and allowed to dry. The static standard protection factor (SPF) was determined. The emulsion was applied to the backs of 7 more voluneers and allowed to dry. The volunteers were then emersed in a whirlpool bath for 40 minutes. After this exposure to rapidly flowing water, the backs were air dried and the SPF was again determined. The results were as follows:

| | |
|---|---|
| Static SPF | 10.45 ± 2.10 |
| SPF after 40 minute exposure to water | 8.79 ± 1.01 |

These results show that the emulsion of Example III is highly substantive.

The emulsion of Example III was also tested on hairless mouse epidermis with the following results:

| Test No. | Static SPF | SPF after 10 minute exposure to running water | SPF after 40 minute exposure to running water |
|---|---|---|---|
| 1 | 15.7 ± 2.8 | 12.5 ± 0.77 | 10.7 ± 0.67 |
| 2 | 15.4 ± 2.2 | 18.6 ± 4.1 | 14.8 ± 3.6 |
| 3 | 14.7 ± 3.4 | 14.5 ± 2.7 | 10.9 ± 1.4 |

Again, a high degree of substantivity was noted.

Numerous other variants of the above formulations will be apparent to one skilled in the art and within the spirit of the invention.

What is claimed is:

1. A dermatologically compatible, highly substantive sunscreening oil-in-water emulsion composition comprising 0.1 to 5% octadecene-1/maleic anhydride copolymer having a molecular weight of 4,000 to 100,000, an effective sunscreening amount of a sunscreening agent, an oil, from 40 to 95% water and having a pH of 6 to 10.

2. A composition according to claim 1 wherein the concentration of said copolymer is 0.3 to 3.0 percent.

3. A composition according to claim 1 in which said copolymer has a molecular weight of about 40,000 to 60,000.

4. A composition according to claim 3 in which the molecular weight of said copolymer is about 50,000.

5. A composition according to claim 1 in which the monomers of said copolymer are present in substantially a 1:2 to 2:1 molar ratio.

6. A composition according to claim 5 in which said monomers are present in substantially a 1:1 molar ratio.

7. A composition according to claim 6 wherein said copolymer has a melting point range of 110°–120°.

8. A composition according to claim 1 in which the composition is an anionic emulsion.

9. A composition according to claim 1 in which the sunscreening agent comprises homomenthyl salicylate.

10. A composition according to claim 1 in which the sunscreening agent comprises octyldimethyl PABA.

11. A composition according to claim 1 in which the sunscreening agent comprises octyl methoxycinnamate.

12. A composition according to claim 1 in which the pH of said composition is 7 to 9.

13. A method of increasing the substantivity of an oil-in-water sunscreening emulsion containing an oil, a sunscreening agent, and 40 to 95% water by incorporating therein 0.1 to 5% of octadecene-1/maleic anhydride copolymer having a molecular weight of 4,000 to 100,000 wherein the pH is 6 to 10.

14. The method of claim 13 wherein the sunscreen agent is selected from the group consisting of octyl dimethyl PABA, homomenthyl salicylate, benzophenone-3, and octyl methoxycinnimate.

* * * * *

UNITED STATES PATENT AND TRADEMARK OFFICE
CERTIFICATE OF CORRECTION

PATENT NO. : 4,522,807

DATED : June 11, 1985

INVENTOR(S) : Carl Kaplan

It is certified that error appears in the above-identified patent and that said Letters Patent is hereby corrected as shown below:

Column 5:
Claim 1 should read as follows:

1. A dermatologically compatible, highly substantive sunscreening oil-in-water emulsion composition comprising 0.01 to 5% octadecene-1/maleic anhydride copolymer having a molecular weight of 4,000 to 100,000 and an effective sunscreening amount of a sunscreening agent in an oil phase, and from 40 to 95% water, said composition having a pH of 6 to 10.

Column 6:

Claim 13 should read as follows:

13. A method of increasing the substantivity of an oil-in-water sunscreening emulsion containing a sunscreening agent in the oil phase, and 40 to 95% water, by incorporating in the oil phase 0.01 to 5% of octadecene-1/maleic anhydride copolymer having a molecular weight of 4,000 to 100,000, wherein the pH is 6 to 10.

Signed and Sealed this

Twenty-ninth Day of September, 1992

Attest:

DOUGLAS B. COMER

*Attesting Officer*         *Acting Commissioner of Patents and Trademarks*

REEXAMINATION CERTIFICATE (2787th)
United States Patent [19]

Kaplan

[11] B1 4,522,807

[45] Certificate Issued Jan. 30, 1996

[54] SUBSTANTIVE TOPICAL COMPOSITIONS

[75] Inventor: Carl Kaplan, Memphis, Tenn.

[73] Assignee: Plough, Inc., Memphis, Tenn.

Reexamination Request:
No. 90/003,824, May 9, 1995

Reexamination Certificate for:
| | |
|---|---|
| Patent No.: | 4,522,807 |
| Issued: | Jun. 11, 1985 |
| Appl. No.: | 496,032 |
| Filed: | May 19, 1983 |
| Filed: | |

Certificate of Correction issued Sep. 29, 1992.

Related U.S. Application Data

[63] Continuation-in-part of Ser. No. 342,304, Jan. 25, 1982, abandoned.

[51] Int. Cl.$^6$ .................... A61K 7/42; A61K 7/44
[52] U.S. Cl. .................... 424/59; 424/47; 424/60; 514/159; 514/543; 514/567

[58] Field of Search .................. 424/47, 59, 69; 514/159, 543, 567

[56] References Cited

U.S. PATENT DOCUMENTS

| | | | |
|---|---|---|---|
| 3,784,488 | 1/1974 | Steinhauer et al. | 260/2.5 M |
| 3,821,363 | 6/1974 | Black et al. | 424/59 |

FOREIGN PATENT DOCUMENTS

| | | | |
|---|---|---|---|
| 0020794 | 1/1981 | European Pat. Off. | 424/59 |
| 1557580 | 12/1979 | United Kingdom | 424/59 |

OTHER PUBLICATIONS

R. Voigt et al., *Lehrbuch der Pharmazeutischen Technologie*, p. 387, Section 23.6.2 (1973)—with English Translation.

*Primary Examiner*—Shelley A. Dodson

[57] ABSTRACT

A highly substantive topical composition in the form of an oil-in-water emulsion containing an octadecene-1/maleic anhydride copolymer.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *